United States Patent [19]

Bajusz et al.

[11] 4,346,078

[45] Aug. 24, 1982

[54] NOVEL ANTICOAGULANT AGMATINE DERIVATIVES AND PROCESS FOR THE PREPARATION THEREOF

[75] Inventors: Sandor Bajusz; Erzsebet Széll nee Hasenöhrl; Éva Barabas; Daniel Bagdy; Zsuzsanna Mohai nee Nagy, all of Budapest, Hungary

[73] Assignee: Richter Gedeon Vegyeszeti Gyar Rt., Budapest, Hungary

[21] Appl. No.: 241,356

[22] Filed: Mar. 6, 1981

[30] Foreign Application Priority Data

Oct. 7, 1980 [HU] Hungary ............................. GO 1449

[51] Int. Cl.$^3$ ..................... A61K 37/00; C07C 103/52
[52] U.S. Cl. ............................... 424/177; 260/112.5 R
[58] Field of Search ................... 424/177; 260/112.5 R

[56] References Cited

PUBLICATIONS

Chem. Abstr. vol. 91, (1979), 207145a; vol. 67, (1967), 84922w.

*Primary Examiner*—Delbert R. Phillips
*Attorney, Agent, or Firm*—Karl F. Ross

[57] ABSTRACT

Anti-coagulants of the formula X-Pro-Agm(HB) $(_n)$ wherein

X is an alpha-amino acid moiety of the configuration having a phenyl, phenyl-(lower)-alkyl or phenyl-(heteroatom-containing) lower alkyl side chain, Agm is an agmatine group (1-amino-4-guanidino-butane), B is an acid residue, and n is an integer from 0–2, are disclosed.

8 Claims, No Drawings

NOVEL ANTICOAGULANT AGMATINE DERIVATIVES AND PROCESS FOR THE PREPARATION THEREOF

The invention relates to novel agmatine derivatives and their salts of formula I, and to a process for the preparation thereof $$X—Pro—Agm.(HB)_n \qquad I$$

wherein

X means an α-amino acid moiety of D-configuration having a phenyl, phenyl-(lower)-alkyl, or phenyl-(heteroatom-containing)lower-alkyl side chain, Pro means, according to the literature (i.e. Biochem. J., 126, 773 1972), an L-proline residue, Agm stands for an agmatine group, B stands for an acid residue, and n means the integer 0, 1 or 2.

It is known that the simple acyl derivatives of agmatine (1-amino-4-guanidino-butane), as for instance tosyl-agmatine (1-[p-toluene-sulfonylamido]-4-guanidino-butane), have the ability to inhibit the proteolytic reactions of both tripsin and thrombin (Lorand and Rule: Nature, 190, 722, 1961; Rule and Lorand: Biochim. Biophys. Acta, 81, 130, 1964). According to these authors tosyl-agmatine delays the clotting of blood plasma, and also is assumed to suppress the fibrinogen-thrombin reaction. In our own experiments, however, the fibrinogen-thrombin reaction was affected by tosyl-agmatine to a negligible degree: 0.7 mg of tosyl-agmatine is required to double (from 15 sec to 30 sec) the thrombin time of 1 ml of a solution containing 1.25 mg of fibrinogen and 1.25 NIH units of thrombin ("Minimum Requirements of Dried Thrombin", 2nd rev. Div. Biol. Conf. Natl. Inst. Health, Bethesda, Md., United States 1946).

It is the object of the present invention to prepare novel agmatine derivatives exhibiting enhanced anticoagulant activity.

It was found that the new dipeptidyl derivatives of agmatine of formula I exhibit significant anticoagulant potency. It is especially favorable if the side chain of the N-terminal D-α-amino acid moiety of the dipeptidyl-agmatine is a phenyl-lower-alkyl group; thus the D-phenyla-lanyl-L-prolyl-agmatine has extremely high activity.

Table 1 demonstrates the effect of the novel agmatine derivatives of the invention of formula I, and of the known tosyl-agmatine on the fibrinogen-thrombin reaction. The potency of the substances is defined by the amount of the compound required to double the thrombin time of fibrinogen. Furthermore, the relative potency of the novel agmatine derivatives related to tosyl-agmatine (the activity of the last-mentioned drug is taken as unity) is listed, too.

The potency of the compounds was assayed in the following system:

0.2 ml of 0.5 percent bovine fibrinogen in 0.9 percent NaCl solution, 0.1 ml of tris-(hydroxymethyl)-methylamine hydrochloride buffer solution (pH=7.4) containing the agmatine derivative, and 0.1 ml US Standard Human Thrombin 5 NIH Unit/ml. The thrombin time of the system devoid of agmatine derivative is 15 seconds.

TABLE 1

Amount of agmatine derivative required to double the thrombin-time of fibrinogen

| Derivative* | μ/ reaction mixture | relative activity |
|---|---|---|
| H—D—Phg—Pro—Agm | 1.4 | 200 |
| H—D—Ser(Bzl)—Pro—Agm | 0.7 | 400 |
| H—D—Phe—Pro—Agm | 0.12 | 2333 |
| Tosyl—agmatine | 280 | 1 |

*The abbreviations used for amino acid residues and peptide derivatives in the Table and in the following conform to the literature (Biochem. J., 126, 773 1972), furthermore Phg means phenyl-glycin, Agm = agmatine, and Bzl, Z and Boc stand for benzyl, benzyloxycarbonyl, and tert-butyloxycarbonyl groups, respectively. The —D—Ser/Bzl/ group means an O—benzyl—D—serineresidue.

It was found, furthermore, that the anticoagulant effect of the novel dipeptidyl-agmatine derivatives of formula I is enhanced by commercial heparin used for therapeutic purposes, which can be confirmed in both in vitro and in vivo experiments.

In in vitro trials the effect of D-Phe-Pro-Agm.2HCl (in formula I, X is a D-phenylalanine moiety, B is chloride ion and n=2) and heparin was studied in an isolated system, in a fibrinogen-thrombin reaction mixture A and in human citrate plasma B:

A:

0.2 ml of 0.5 percent bovine fibrinogen in 0.9 percent saline solution, 0.1 ml of a tris-(hydroxymethyl)-methylamine hydrochloride buffer (pH=7.4), containing the agmatine derivative and/or heparin (132.2 U/mg U.S.Ph. XVII), and 0.1 ml US Standard Human Thrombin 10 NIH Unit/ml.

The thrombin-time of the system devoid of inhibitor is 15 seconds.

B:

0.2 ml of human citrate plasma 0.1 ml of tris-(hydroxymethyl)-methylamine hydrochloride buffer (pH=7.4), containing the agmatine derivative and/or heparin (132.2 U/mg U.S.Ph. XVII), and 0.1 ml US Standard Human Thrombin 10 NIH U/ml.

The thrombin-time of the system devoid of inhibitor is 15 seconds. The results are summarized in Table 2, demonstrating how the thrombin-time is prolonged by each drug alone and by a combination of them in systems A and B, resp., and the thrombin time calculated on the basis of individual potencies (the thrombin-time devoid of inhibitor is taken as unity).

The daily dose of the compounds of formula I for adults is 50–100 mg/hour when administered in intravenous infusion for 6 to 12 hours/day.

The daily dose of compounds of formula I combined with heparin for adults is 50–60 mg peptide together with 3500–4500 U heparin when administered three or four times per day.

TABLE 2

The anticoagulant effect of D—Phe—Pro—Agm.2 HCl enhanced by heparin in an isolated system /A/ and in human citrate plasma /B/

| | μg/ml reaction mixture | | Relative thrombin-time | | | |
|---|---|---|---|---|---|---|
| | | | alone | | D—Phe—Pro—Agm + Heparin | |
| | D—Phe—Pro—Agm* | Heparin | D—Phe—Pro—Agm* | Heparin | calculated | assayed |
| A | 0.10 | 0.05 | 2.5 | 1.1 | 2.6 | 4.0 |
| | 0.10 | 0.10 | 2.5 | 1.5 | 3.0 | 6.0 |
| | 0.10 | 0.20 | 2.5 | 2.0 | 3.5 | 9.0 |
| | 0.20 | 0.05 | 4.0 | 1.1 | 4.1 | 7.5 |
| | 0.20 | 0.10 | 4.0 | 1.5 | 4.5 | 13.0 |
| | 0.20 | 0.20 | 4.0 | 2.0 | 5.0 | 22.0 |
| B | 0.05 | 0.05 | 2.2 | 1.0 | 2.2 | 4.0 |
| | 0.05 | 0.10 | 2.2 | 2.0 | 3.2 | 6.2 |
| | 0.05 | 0.20 | 2.2 | 3.8 | 5.0 | 9.5 |
| | 0.10 | 0.05 | 3.4 | 1.0 | 3.4 | 7.8 |
| | 0.10 | 0.10 | 3.4 | 2.0 | 4.4 | 13.0 |

*D—Phe—Pro—Agm.2 HCl

In in vivo trials gray rabbits (2 to 3 kg) were administered subcutaneously:

a. 5 mg/kg heparin (132.2 U/mg U.S.Ph. XVII),
b. 10 mg/kg D-Phe-Pro-Agm.2HCl, or
c. 5 mg/kg heparin and 10 mg/kg D-Phe-Pro-Agm.2HCl.

Following administration of the drugs blood samples were withdrawn from the ear vein of the rabbits every thirty minutes and the thrombin-time of the whole blood determined in a thromboelastograph (Hartert, H.: Zschr. f. clin. Med. 153, 423, 1955). In the course of the experiments it was apparent that both heparin and the agmatin derivative alone exhibit only slight activity at the dose levels applied (a and b); the thrombin-time of the complete blood is prolonged a mere 1.5 fold (relative thrombin-time is 1.2 to 1.5 at best), also the prothrombin activity of the blood is practically unaltered. If the agmatine derivative was administered together with heparin in the same doses (c), an enhanced anticoagulant effect was registered in the experimental animals, the relative thrombin-time was 4 to 5 fold for 3 to 4 hours in the self control experiments. At the same time the prothrombin activity of the blood samples taken at various intervals and assayed according to Quick (Quick, A. J.: J. Biol. Chem. 109, 73, 1935) was reduced from the 100 percent level, prior to treatment, to 20 to 30 percent. This value may be considered, according to the literature, as an anticoagulant effect of therapeutic value.

The invention also involves a process for preparing novel agmatine derivatives of formula I, wherein X, Pro, Agm, B and n have the meanings mentioned above, by condensing a 1,4-diamino-butane derivative of formula II:

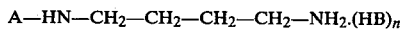

$$A-HN-CH_2-CH_2-CH_2-CH_2-NH_2 \cdot (HB)_n \quad \text{II}$$

wherein A is a $H_2N-C(NH)-$, $Y-HN-C(NH)-$ or Q moiety, Y and Q are amino protecting groups usually applied in peptide chemistry, B is an acid residue and n is 0, 1 or 2—with an L-proline blocked on its amino group and stepwise with the subsequent amino acid, or with some L-proline-peptide, by known methods of peptide chemistry. The Q protecting group is optionally cleaved from the 1,4-diamino-butane moiety of the compound prepared, the amino group, set free, is converted into a guanidino group by known methods, from the resulting dipeptidyl-agmatine both the terminal amino protecting group and optionally the Y blocking group of the guanidino moiety are removed and the free dipeptidyl-agmatine is isolated in the form of a salt.

According to the present invention, compounds of formula I, where X stands for a D-phenylalanine residue, are preferably prepared by forming from Z-D-Phe-Pro-OH (Nikolaides et al.: J. Med. Chem., 11, 74, 1968) and chloroformic acid alkyl ester a mixed anhydride, and this is reacted with agmatine hydrochloride (in formula II A means an $H_2N-C(NH)-$ group, B a chlorine atom and n=1), or with an agmatine having a benzyloxycarbonyl (Z) group on its guanidino group (in formula II A means $Y-HN-C(NH)-$ group, Y a Z group and n=0), the Z protecting group or groups are cleaved from the blocked dipeptidyl-agmatine formed, and D-Phe-Pro-Agm is isolated in the form of a salt.

According to the present invention one can also proceed by condensing 4-(tert-butyloxycarbonylamido)-butylamine (in formula II A=Q stands for a tert-butyloxycarbonyl(Boc) group, and n=0), see Geiger: Liebigs Ann. Chem., 750, 165, 1971), with benzyloxycarbonyl-L-proline by a known method (Fuchs et al.: Liebigs Ann. Chem., 1977, 602), the Boc group is cleaved from the condensate, the amino group, set free, is converted into a guanidino group, the Z group is removed from the Z-Pro-Agm-Z formed, then an α-amino acid, having a suitable protective group at its amino group (i.e. Boc-D-Ser(Bzl)-OH, Z-D-Phg-OH), is coupled to the Pro-Agm, and finally the terminal amino protective group is removed from the dipeptidyl-agmatine, and the free dipeptidyl-agmatine is isolated in the form of a salt.

The following Examples are illustrative of the invention.

The $R_F$ values were determined by silica gel thin-layer chromatography (Kieselgel G. REANAL, Budapest) in the following solvent systems:

1. chloroform-methanol—9:1
2. ethyl acetate-pyridine—acetic acid-water—240:20:6:11
3. ethyl acetate-pyridine-acetic acid-water—60:20:6:11
4. ethyl acetate-pyridine-acetic acid-water—30:20:6:11.

EXAMPLE 1

D-Phenylalanyl-L-prolyl-agmatine-dichlorohydrate (in formula I X represents a D-phenylalanine residue, B a chlorine atom and n=2)

Step 1: -Benzyloxycarbonyl-S-methyl-isothiourea 13.9 g (0.1 mole) of S-methyl-isothiourea are dissolved in 50 ml of water, cooled to a temperature of 0° to 5° C., and at this temperature and with constant stirring 15 ml (0.1 mole) of chloroformic acid benzyl ester and 50 ml of 4 N sodium hydroxide are added in about 20 minutes. The precipitate formed is filtered, washed three times with 50 ml of cold water, then three times with 50 ml of n-hexane, and finally dried over phosphorpentoxide in vacuo. Yield 15.7 g (70 percent) of the named compound. M.p.: 74° to 75° C.; $R_F^1$ 0.70 to 0.75.

$C_{10}H_{12}O_2N_2S$ (molecular weigh=224.27).

Calculated: C: 53.55, H: 5.39 N: 12.49 S: 14.3 percent; Found: C: 53.59, H: 5.69, N: 12.23, S: 14.27 percent.

Step 2:
N-Tert-butyloxycarbonyl-$N^G$-benzyloxycarbonyl-agmatine 6.7 g (30 mole) of 1-(tert-butyloxycarbonyl)-1,4-diamino-butan-hydrochloride (Geiger: Liebigs Ann. Chem., 750, 165, 1971) and 6.7 g (30 mmoles) of the isothiourea derivative (Example 1, Step 1) are dissolved in 15 ml of ethanol, 4.2 ml (30 mmoles) of triethylamine added, and the solution kept for 3 hours on a steam bath. The reaction mixture is evaporated, the residue dissolved in a mixture of 150 ml of benzene and 50 ml of 1 N acetic acid, the benzene layer washed with 10 ml of water and evaporated at reduced pressure. The crystalline residue is suspended in 30 to 50 ml of benzene cooled to about 10° C., filtered, and washed with 10 ml of cool benzene, then with n-hexane. Yield 7.9 g (60 percent) of the named compound. M.p.: 99° to 101° C.; $R_F^1$ 0.60 to 0.64.

$C_{18}H_{28}O_4N_4 \cdot CH_3COOH \cdot \frac{2}{3}H_2O$ (m.w.=436.5).

Calculated: C: 55.03, H: 7.69 N: 12.84 percent Found: C: 55.1, H: 7.8, N: 12.65 percent.

Step 3:
$N^G$-Benzyloxycarbonyl-agmatine-dichlorohydrate (in formula II A stands for a Y—HN—C(NH) moiety, Y for a benzyloxycarbonyl group, B means a chlorine atom, and n=2)

5.5 g (15 mmoles) of protected agmatine (Example 1, Step 2) are suspended in 10 ml of ethyl acetate, then at stirring and ice cooling 20 ml of ethyl acetate, containing 11 to 15 percent hydrochloric acid are added. Stirring is continued for 30 minutes, then the suspension is diluted with 10 ml of ethyl acetate, filtered, washed with ethyl acetate, and dried over potassium hydroxide at room temperature and at reduced pressure. Yield: 4.3 g (83 percent) of the named compound. M.p.: 150° to 153° C.; $R_F^4$ 0.49 to 0.59.

$C_{13}H_{20}O_2N_4 \cdot 2HCl \cdot \frac{1}{3}H_2O$ (m.w.=343.3).

Calculated: C: 45.48, H: 6.65, N: 16.32, Cl: 20.65 percent; Found: C: 45.5, H: 6.5, N: 16.3, Cl: 20.3 percent.

Step 4:
Benzyloxycarbonyl-D-phenylalanyl-L-prolyl-$N^G$-benzyloxycarbonyl-agmatine 2 g (6 mmoles) of blocked agmatine-hydrochloride (Example 1, Step 3) are suspended in 10 ml of dimethylformamide, 1.5 ml of water added, then the pH of the solution is adjusted to 8 to 9 with triethylamine (about 1.5 ml). The solution is cooled to −15° C., and poured into the following mixed anhydride: 2.4 g (6 mmoles) of benzyloxycarbonyl-D-phenylalanyl-L-proline (Nikolaides et al.: J. Med. Chem., 11, 74, 1968) are dissolved in 12 ml of dimethylformamide, cooled to −15° C., and at this temperature and at stirring 0.66 ml (6 mmoles) of N-methyl-morpholine and 0.8 ml (6 mmoles) of chloroformic acid isobutyl ester are added. After stirring for 10 minutes the above dimethylformamide solution is poured into it. The pH of the reaction mixture is adjusted, if necessary, to 8 to 9 with triethylamine, and the stirring is continued for 1 hour at −15° C. and for 1 hour at 0° C., then the reaction mixture is evaporated. The residue is dissolved in a mixture of 60 ml of a 4:1 benzene-ethyl acetate solution and 20 ml of water, the organic layer washed twice with 20 ml of water containing 1 percent of morpholine, twice with 20 ml of 0.1 N hydrochloric acid, and finally twice with 20 ml of water, dried over sodium sulfate, and evaporated at reduced pressure. Yield: 3.1 g (80 percent) of the named compound. $R_F^2$ 0.30 to 0.35.

Step 5:
D-Phenylalanyl-L-prolyl-agmatine-dihydrochloride 3.1 g (4.8 mmoles) of protected dipeptidylagmatine (Example 1, Step 4) are dissolved in 40 ml of methanol, 4.8 ml of 2 N hydrochloric acid added, and the mixture hydrogenated over palladium-charcoal. When the reaction is concluded, the catalyst is filtered, washed with water, and the filtrate evaporated at reduced pressure. The residue is dissolved in 5 ml of methanol and diluted with 30 to 40 ml of acetone. The crystals formed are filtered, washed with acetone and air-dried. Yield 2.05 g (95 percent) of the named compound. M.p.: 216° to 219° C.; $R_F^4$ 0.5 to 0.6; $[\alpha]_D^{20} = -125.5°$ (c=1, 0.1 N acetic acid).

$C_{19}H_{30}O_2N_6 \cdot 2HCl \cdot \frac{1}{3}H_2O$ (m.w.=453.4).

Calculated: C: 50.32, H: 7.26, N: 18.53, Cl: 15.64 percent Found: C: 50.8, H: 7.5, N: 18.3, Cl: 15.6 percent.

EXAMPLE 2

D-Phenylalanyl-L-prolyl-agmatine-dihydrochloride (in formula I X represents a D-phenylalanine residue, B a chlorine atom and n=2).

Step 1:
Benzyloxycarbonyl-D-phenylalanyl-L-prolyl-agmatine-chlorohydrate 4 g (10 mmoles) of benzyloxycarbonyl-D-phenylalanyl-L-proline (Nikolaides et al.: J.Med.Chem., 11, 74, 1968) are dissolved in 20 ml of dimethylformamide, cooled to −15° C., and at this temperature and constant stirring 1.11 ml (10 mmoles) of N-methyl-morpholine and 1.32 ml (10 mmoles) of chloroformic acid isobutyl ester are added. Stirring is continued for 10 minutes when the following solution is poured into it: 2.05 g (10 mmoles) of agmatine-dichlorohydrate (in formula II A means an $H_2N$—C(NH)— residue, B a chlorine atom and n=2) are suspended in 15 ml of dimethylformamide, 2 ml of water, then 1.4 ml (10 mmoles) of triethylamine are added, and cooled to −15° C. The reaction mixture is stirred for 2 hours at −15° C., for 1 hour without cooling, then is evaporated at reduced pressure. The evaporation residue is dissolved in 100 ml of 0.2 N hydrochloric acid and extracted three times with 20 ml of ethyl acetate. The pH of the aqueous layer is adjusted with solid sodium hydrogen carbonate to 8.0 to 8.5, and extracted five times with 20 ml of chloroform. The combined chloroform layers are washed twice with 10 ml of water, and evaporated at reduced pressure. The residue is worked up with diethyl ether, filtered, washed with diethyl ether and air-dried. Yield: 4.1 g (75 percent) of the named compound. $R_F^3$ 0.5 to 0.6.

Step 2:
D-phenylalanyl-L-prolyl-agmatine-dichlorohydrate 3.8 g (7 mmoles) of blocked dipeptidyl-agmatine (Example 2, Step 1) are dissolved in 60 ml of methanol, 3.5 ml of 2 N hydrochloric acid added, and the mixture hydrogenated over palladium charcoal. When the reaction is concluded, the catalyst is filtered, washed with water, and the filtrate evaporated at reduced pressure. The residue is dissolved in 10 ml of methanol, and diluted with 40 to 60 ml of acetone. The crystals formed are filtered, washed with acetone and air-dried. Yield: 2.95 g (95 percent) of the named product. M.p.: 216° to 219° C.; $R_F^4$ 0.5 to 0.6; $[\alpha]_D^{20} = -125.5°$ (c=1, 0.1 N acetic acid).

EXAMPLE 3

O-Benzyl-D-seryl-L-prolyl-agmatine-dichlorohydrate (in formula I X stands for an O-benzyl-D-serine residue, B for a chlorine atom and n=2)

Step 1: L-prolyl-agmatine-dichlorohydrate 3.7 g (10 mmoles) of benzyloxycarbonyl-L-prolyl-p-nitrophenyl ester (Goodman and Stueben: J. Am. Chem. Soc., 81, 3980, 1959) are dissolved in a mixture of 10 ml of dimethylformamide and 5 ml of pyridine, 2.03 g (10 mmoles) of agmatine-dichlorohydrate (in formula II A represents an $H_2N-C(NH)-$ residue, B a chlorine atom and n=2) and 1.4 ml (10 mmoles) of triethylamine added, and stirred for 16 to 20 hours. The reaction mixture is evaporated at reduced pressure. The residue is dissolved in a mixture of 50 ml of 0.1 N hydrochloric acid and 20 ml of ethyl acetate, the aqueous layer is extracted twice with 20 ml of diethyl ether, neutralized with solid sodium hydrogen carbonate and then extracted five times with 20 ml of chloroform. The combined chloroform layers are washed twice with water and evaporated at reduced pressure. The evaporation residue, benzyloxycarbonyl-L-prolyl-agmatine-hydrochloride ($R_F^3$ 0.32 to 0.42), is dissolved in 40 ml of methanol, 10 ml of 1 N hydrochloric acid added, and the mixture hydrogenated in the presence of palladium charcoal. When the reaction is concluded, the catalyst is filtered, washed with water, and the filtrate evaporated at reduced pressure. The evaporation residue is worked up with diethyl ether, filtered, washed with diethyl ether and dried over potassium hydroxide at reduced pressure. Yield: 2.1 g (70 percent) of the named compound. M.p.: 186° to 189° C.; $R_F^4$ 0.15 to 0.25; $[\alpha]_D^{20} = -33.25°$ (c=1, methanol).

$C_{10}H_{21}ON_2.2HCl$ (m.w.=300.2).

Calculated: C: 40.00, H: 7.72, N: 23.32, Cl: 23.62 percent; Found: C: 40.00, H: 7.7, N: 23.0, Cl: 23.3 percent.

Step 2:
O-Benzyl-D-seryl-L-prolyl-agmatine-dichlorohydrate 1.5 g (5 mmoles) of L-prolyl-agmatine-dichlorohydrate (Example 3, Step 1) are suspended in 5 ml of dimethylformamide, 0.5 ml of water and 0.7 ml (5 mmoles) of triethylamine added, the mixture is cooled to −15° C. and poured into the following mixed anhydride: 1.5 g (5 mmoles) of tert-butyloxycarbonyl-O-benzyl-D-serine (Otsuka et al.: Bull. Chem. Soc. Japan, 39, 1171, 1966) are dissolved in 10 ml of dimethylformamide, cooled to −15° C., and at this temperature and at stirring 0.6 ml (5 mmoles) of N-methyl-morpholine and 0.7 ml (5 mmoles) of chloroformic acid-isobutyl ester added. Stirring is continued for 10 minutes, then the above dimethylformamide solution is poured into it.

The reaction mixture is stirred for one hour at −15° C., then for a further hour at 0° C., and is finally evaporated at reduced pressure. The residue is dissolved in a mixture of 10 ml of water and 50 ml of chloroform, the chloroform layer washed twice with 10 ml of water and twice with 10 ml of a 5 percent sodium hydrogen carbonate solution, dried over sodium sulfate and evaporated at reduced pressure. The residue is worked up with diethyl ether, filtered, washed with diethyl ether and air-dried. The resulting tert-butyloxycarbonyl-O-benzyl-D-seryl-L-prolyl-agmatine-hydrochloride ($R_F^3$ 0.4 to 0.5) is suspended in 5 ml of ethyl acetate, and at constant stirring and ice-cooling 10 ml 11 to 15 percent hydrochloric acid containing ethyl acetate are added. After stirring for 30 minutes the suspension is filtered, washed with ethyl acetate and dried over potassium hydroxide at reduced pressure. The product is dissolved in 20 ml of water, and freeze-dried. Yield: 1.62 g (65 percent) of the named product. M.p.: 110° to 115° C.; $R_F^4$ 0.56 to 0.66; $[\alpha]_D^{20} = -47°$ (c=1, 0.1 N acetic acid).

$C_{20}H_{32}O_3N_6.2HCl.H_2O$ (m.w.=495.45).

Calculated: C: 48.48, H: 7.32, N: 16.96, Cl: 14.31 percent; Found: C: 48.4, H: 7.4, N: 16.85, Cl: 14.3 percent.

EXAMPLE 4

D-Phenylglycyl-L-prolyl-agmatine-dichlorohydrate (in formula I X represents a D-phenylglycine residue, B a chlorine atom, and n=2)

Step 1: 1-Amidino-3,5-dimethyl-pyrazol-acetate 20.1 g (100 mmoles) of 1-amidino-3,5-dimethyl-pyrazol-nitrate (Thiele and Dralle: Ann., 302, 294, 1898) are dissolved in 200 ml of methylenechloride and 110 ml of 1 N sodium hydroxide. The aqueous layer is extracted twice with 50 ml of methylene chloride, the methylene chloride solutions are combined, dried over sodium sulfate, acidified with acetic acid (about 6 ml), and evaporated at reduced pressure. The crystalline residue obtained is suspended in diethyl ether, filtered, washed with diethyl ether and air-dried. Yield: 18.25 g (92 percent) of the named product. M.p.: 114° to 116° C.

$C_6H_{10}N_4.CH_3COOH$ (m.w.=198.2).

Calculated: C: 48.47, H: 7.12, N: 28.27 percent; Found: C: 48.6, H: 7.1, N: 28.5 percent.

Step 2: L-Prolyl-agmatine-dichlorohydrate 4.2 g (10 mmoles) of benzyloxycarbonyl-L-prolyl-4-(tert-butyloxycarbonylamido)-butylamine (Fuchs et al.: Liebigs Ann. Chem., 1977, 602) are suspended in 10 ml of ethyl acetate, then at constant stirring and ice-cooling 20 ml of ethyl acetate containing 11 to 15 percent hydrochloric acid are added. After stirring for 30 minutes the suspension is filtered, washed with ethyl acetate and dried over potassium hydroxide at reduced pressure. The resulting product ($R_F^3$ 0.24 to 0.34) is dissolved in 10 ml of ethanol, 2 g (10 mmoles) of 1-amidino-3,5-dimethyl-pyrazolacetate (Example 4, Step 1) and 1.4 ml (10 mmoles) of triethylamine added, then the reaction mixture is kept for 3 hours on a steam bath. Then the solution is evaporated at reduced pressure, worked up with ethyl acetate, filtered, and washed with ethyl acetate and diethyl ether. The resulting benzyloxycarbonyl-L-prolyl-agmatine-chlorohydrate ($R_F^3$ 0.3 to 0.4) is dissolved in 40 ml of methanol, 10 ml of 1 N hydrochloric acid added, and the mixture hydrogenated in the presence of palladium charcoal. At concluded reaction the catalyst is filtered, washed with water, and the filtrate evaporated at reduced pressure. The evaporation residue is worked up with diethyl ether, the crystals formed filtered, washed with diethyl ether, and air-dried. Yield 1.81 g (60 percent) of L-prolyl-agmatine-dichlorohydrate. M.p.: 186° to 189° C.; $R_F^4$ 0.15 to 0.25.

Step 3:
D-Phenylglycyl-L-prolyl-agmatine-dichlorohydrate 1.43 g (5 mmoles) of benzyloxycarbonyl-D-phenylglycine (Wissmann et al.: Z. Physiol. Chem., 355, 1083 1974) are converted into a mixed anhydride, and made to react with 1.5 g (5 mmoles) of L-prolyl-agmatine-dichlorohydrate (Example 3, Step 1, or Example 4, Step 2) according to the procedure described in Example 3, Step 2. The benzyloxycarbonyl-D-phenylglycyl-L-prolyl-agmatine-hydrochloride, obtained by working up the reaction mixture ($R_F^3$ 0.28 to 0.34), is dissolved in 30 ml of methanol, 5 ml of 1 N hydrochloric acid added, and the mixture submitted to hydrogenation in the presence of palladium charcoal. By the end of the reaction the catalyst is filtered, washed with water, and the filtrate evaporated at reduced pressure. The residue is worked up with ether, filtered, washed with diethyl ether and dried over potassium hydroxide at reduced pressure. Yield: 1.62 g (75 percent) of the named product. $R_F^3$ 0.2 to 0.2; $R_F^4$ 0.43 to 0.50; $[\alpha]_D^{20} = -94°$ (c=1, 0.1 N acetic acid).

What we claim is:

1. An agmatine compound or a pharmaceutically effective salt thereof of the formula I:

$$X—Pro—Agm·(HB)_n$$

wherein
X is an α-amino acid moiety of D-configuration, having a phenyl, phenyl-lower-alkyl, or phenyl-lower alkyl wherein the lower alkyl is interrupted by an oxygen atom,
Pro is an L-proline residue,
Agm is an agmatine group,
B is chloride and
n is 0, 1 or 2.

2. The compound or salt defined in claim 1 wherein X is a D-α-amino acid moiety having a phenyl-lower-alkyl group.

3. The compound or salt defined in claim 2 which is D-phenylalanyl-L-prolyl-agmatine·(HB)$_n$.

4. The compound or salt defined in claim 1 which is D-phenylglycyl-L-prolyl-agmatine·(HB)$_n$.

5. The compound or salt defined in claim 1 which is O-benzyl-H-D-seryl-L-prolyl-agmatine·(HB)$_n$.

6. An anticoagulant pharmaceutical preparation containing an effective amount of at least one compound or salt of formula I as defined in claim 1 together with a pharmaceutical vehicle in a dosage form.

7. The composition defined in claim 6 which further comprises 50 to 100 units of pharmaceutical grade heparin per 1 mg of peptide.

8. An anticoagulant method of treatment which comprises the step of administering to a mammalian patient an effective amount of a compound or salt as defined in claim 1.

* * * * *